United States Patent [19]

Berceaux

[11] Patent Number: 5,125,833
[45] Date of Patent: Jun. 30, 1992

[54] PROSTHETIC POSITIONING DEVICE FOR DENTISTRY

[76] Inventor: Pierre Berceaux, 39 boulevard Henri Henrot, F-51100 Reims, France

[21] Appl. No.: 635,579
[22] PCT Filed: Mar. 27, 1990
[86] PCT No.: PCT/FR90/00206
§ 371 Date: Jan. 22, 1991
§ 102(e) Date: Jan. 22, 1991
[87] PCT Pub. No.: WO90/11056
PCT Pub. Date: Oct. 4, 1990

[30] Foreign Application Priority Data

Mar. 28, 1989 [FR] France .................. 89 03977
Sep. 14, 1989 [FR] France .................. 89 12062

[51] Int. Cl.⁵ ..................................... A61C 19/00
[52] U.S. Cl. .......................... 433/74; 433/34; 433/313
[58] Field of Search ............... 433/213, 74, 53, 34

[56] References Cited

U.S. PATENT DOCUMENTS

| | | | |
|---|---|---|---|
| 3,153,283 | 10/1964 | Weissman | 433/74 |
| 3,798,772 | 3/1974 | Eberhard | 433/74 |
| 4,056,585 | 11/1977 | Waltke | 433/74 |
| 4,240,605 | 12/1980 | Waltke | 249/54 |
| 4,721,464 | 1/1988 | Roden et al. | 433/213 |
| 4,801,264 | 1/1989 | Weissman | 433/74 |

FOREIGN PATENT DOCUMENTS

| | | |
|---|---|---|
| 0317397 | 11/1988 | European Pat. Off. |
| 1566194 | 8/1970 | Fed. Rep. of Germany |
| 3103637 | 2/1981 | Fed. Rep. of Germany |
| 8600632 | 8/1986 | Fed. Rep. of Germany |
| 2157331 | 6/1973 | France |
| 2623081 | 11/1987 | France |
| 8906114 | 7/1989 | PCT Int'l Appl. |
| 866118 | 4/1961 | United Kingdom |

*Primary Examiner*—Cary E. O'Connor
*Attorney, Agent, or Firm*—Pearne, Gordon, McCoy & Granger

[57] ABSTRACT

The invention relates to a prosthetic positioning device for making removable portions of prosthetic prints and for producing them by single phase casting. The positioning device is comprised essentially of a positioning element (110) supporting the positive part of the print through a pivot with retaining throat (111) nested in a tapered element (20) integral with the positive print via two lugs (21) and two pins (3) used to immobilize the assembly with respect to the negative print via tongues (12) extending from the positioning element (10).

4 Claims, 4 Drawing Sheets

PROSTHETIC POSITIONING DEVICE FOR DENTISTRY

The invention concerns a prosthetic positioning device designed to render portions of prosthetic impressions immobile and to produce prosthetic impressions by one-step pouring.

The technique used until now to make a dental mole consisted of filling the impression with a molding material, then turning it over onto a pile of the same material (most often plaster) or even putting the impression in a standard mold that had been pre-filled with the complementary material.

However, this practice becomes rather delicate when it must be used with a resin-based material that must be poured in liquid form, which makes it impossible to turn the impression over.

At the present time, we therefore resort mainly to a system of different shaped posts or to the technique of milling to make the two parts of the mold immobile.

The post system most often uses single or double posts. Interlocking is achieved by attaching them to the impression by pinning, putting them in position in some liquid plaster and marking the place on the impression, or by using a support plate attached to the impression, as described in French patent 2.157.331. However, these techniques do not make the immobile elements parallel; they are therefore reserved for isolated jobs or those that are not very important.

The milling technique makes it possible to mitigate the fact that the immobile elements are not parallel, which represents a major handicap in making ceramics bridges and doing other precision work. The technique consists of pouring to produce a mold whose base is flat so that milling can be done before the posts, which may be sheathed, are installed. These posts are immersed in a new mold, after the primary mold has been isolated using a layer of varnish.

The elements are then rendered immobile by sawing, as in the technique previously described. In spite of this, the milling technique has many drawbacks: broken plaster, occlusions of sheaths, etc. It involves a heavy investment and precautions that translate into a huge loss of time.

Devices are already known that make it possible to render portions of prosthetic impressions immobile by cutting them with a saw, such as those described in French patent 2.623.081 and the application for European patent EP 0.317.397.A1. These devices are in the form of plug-in or snap-on systems that make it impossible to bring the parts into close enough contact, which causes dislocations when they are unsnapped and causes scraps to fall into the mold joint, which ruins the result; also, in most cases, the impression must be poured in two steps.

A prosthetic positioning device for dentistry is already known that makes it possible to render portions of prosthetic impressions immobile and to pour them in one step, such as that described in the patent of the Federal Republic of Germany No. DE.A.3.103.637, which is characterized by the use of a snap with a spring button to interlock the two elements with an appropriate interface into which conical posts are implanted.

The metal posts sit in cavities of the same size made of the mold material; so these cavities can become receptacles for foreign bodies, which accumulate under pressure and encrust the material, which makes them very difficult to extract and makes it difficult to position the elements in relation to one another and causes wear and tear on the angles, which translates into looseness.

This invention is aimed at remedying these drawbacks. This invention, as it is characterized, solves the problem, which is to produce a prosthetic positioning device for dentistry that makes it possible to pour an impression quickly with materials that may be fluid, like resins; to obtain immobile elements strictly parallel to one another; to withdraw the prosthetic models made of wax or another soft material easily, as well as the elements on which parts made of delicate material like ceramic are mounted, which can crumble and must consequently be handled carefully with great caution; to control the presence of foreign bodies in the device and to be able to eliminate them easily; and to lend itself to later changes or adaptations by simply being placed on a cut-plaster mold.

The prosthetic positioning device for dentistry according to the invention is characterized mainly by the fact that it consists of a positioning element that supports the positive part of the impression using a post with a retaining groove, which nests into a flared element which is an integral part of the positive impression using two pins and two plugs that are used to immobilize the unit in relation to the negative impression using tongues that extend the positioning element laterally, in which positioning is carried out using a parallelizer equipped with a flexible plastic tip nesting on the flared element, and by the fact that the molding material is retained laterally by a band made of a semi-rigid material.

Provisional joining of the two elements, ensuring that they are in position and hermetically overlapped, is achieved by simple nesting of a male part, in the graded section of the base near the end, in the flared element which is an integral part of the positive impression, pegged using a tenon located at the base of the male part and a mortise in the corresponding side of the flared element.

The male part of the positioning element and the flared element has a rectangular section, whose large sides face the same direction as the tongues that extend the positioning element laterally.

The tongues that extend the positioning element laterally have a trapezoidal section whose small base is located on the side of the post.

The band made of semi-rigid material that holds in the molding material is fixed in the modeling clay with pointed pins evenly distributed along one side of the band.

The ends of the band made of semi-rigid material can be joined using slots that are half as long as the width of the band, each made in one side of the band so the ends of the band can be joined by simply inserting them into the right slot.

According to one preferred method of execution of the invention, the positioning element and the flared element are made of a rigid plastic material.

The advantages gained from this invention basically consist of the fact that: pouring is done in a single operation because of the band which serves as a liner; once the positioning element is rendered immobile, it is guided perfectly and repositioned by the element in which it is nesting which remains on the mold; the elements can be assembled using a parallelizer with an appropriate tip; no matter how many prosthetic models there are, they can be withdrawn simultaneously and joined using tongues provided for that purpose; and the footing of the posts can take shapes appropriate to those of the maxillaries, while the parts used for nesting retain the same shape and the same dimensions.

Other characteristics and advantages will appear in the following description of a prosthetic positioning device made according to the invention, which is given as a nonlimiting example, with regard to the appended drawings on which:

Figure 1:
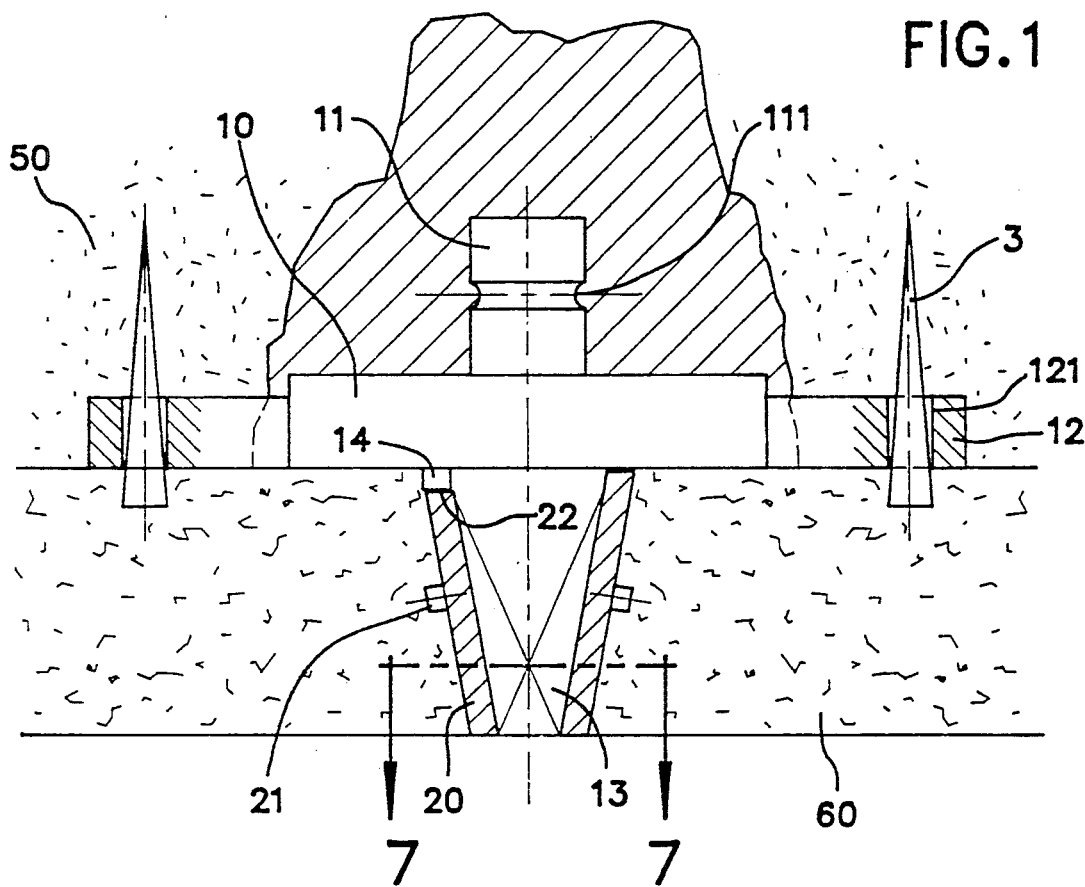
FIG. 1 shows a longitudinal section of the mounted unit.
Figure 2:
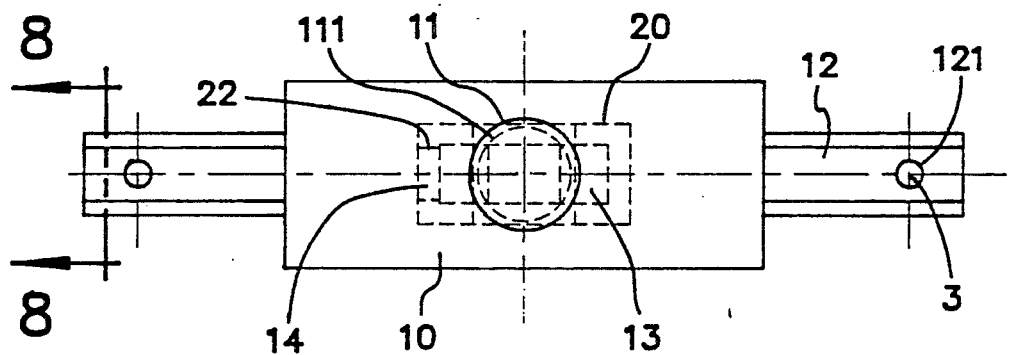
FIG. 2 shows an overview of the mounted unit.
Figure 3:
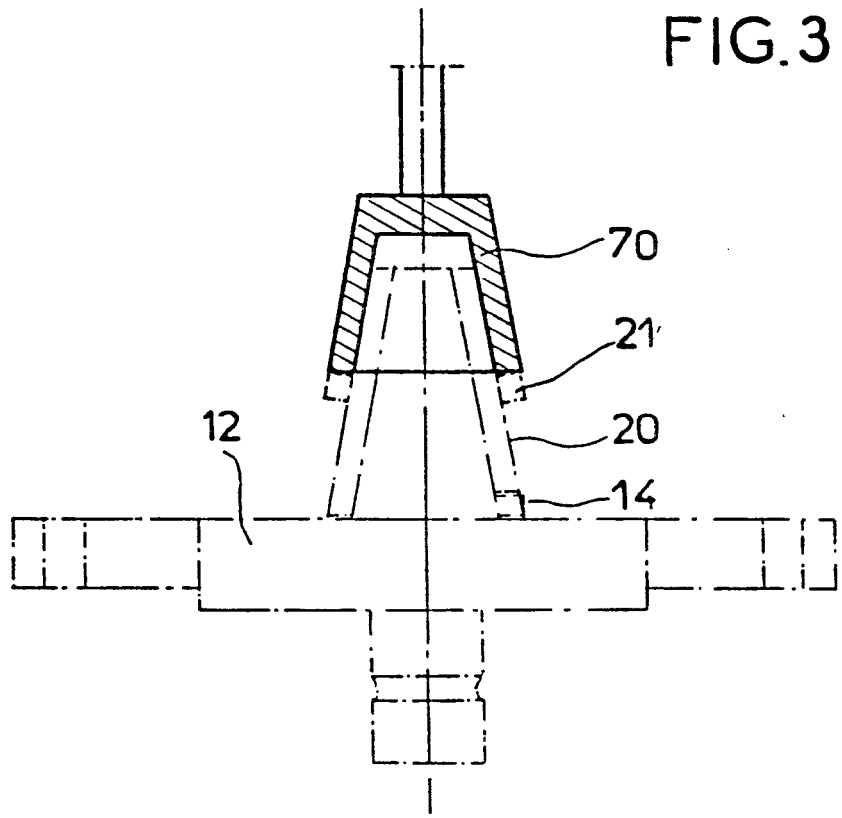
Figure 4:
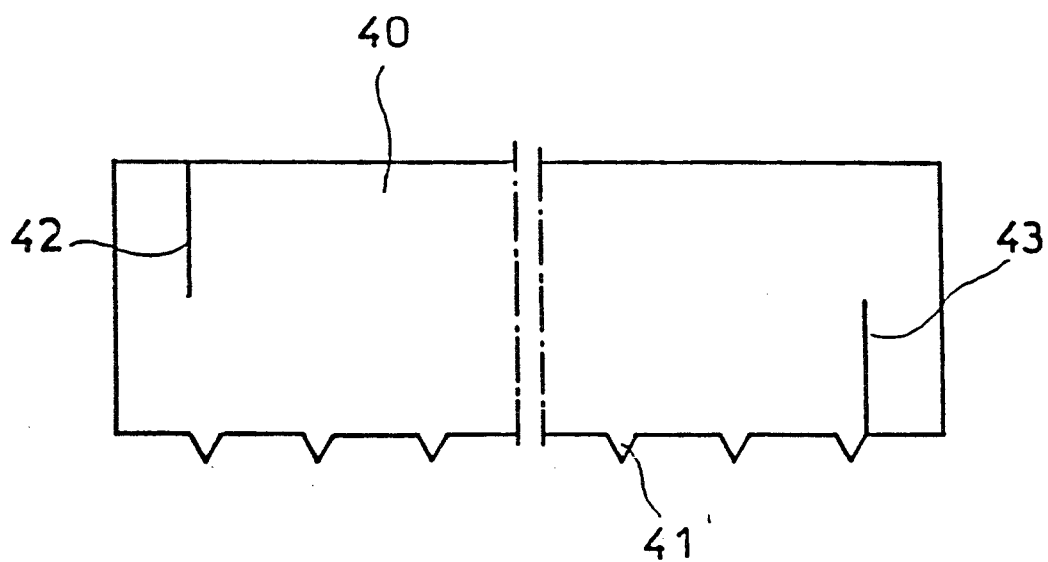
Figure 5:
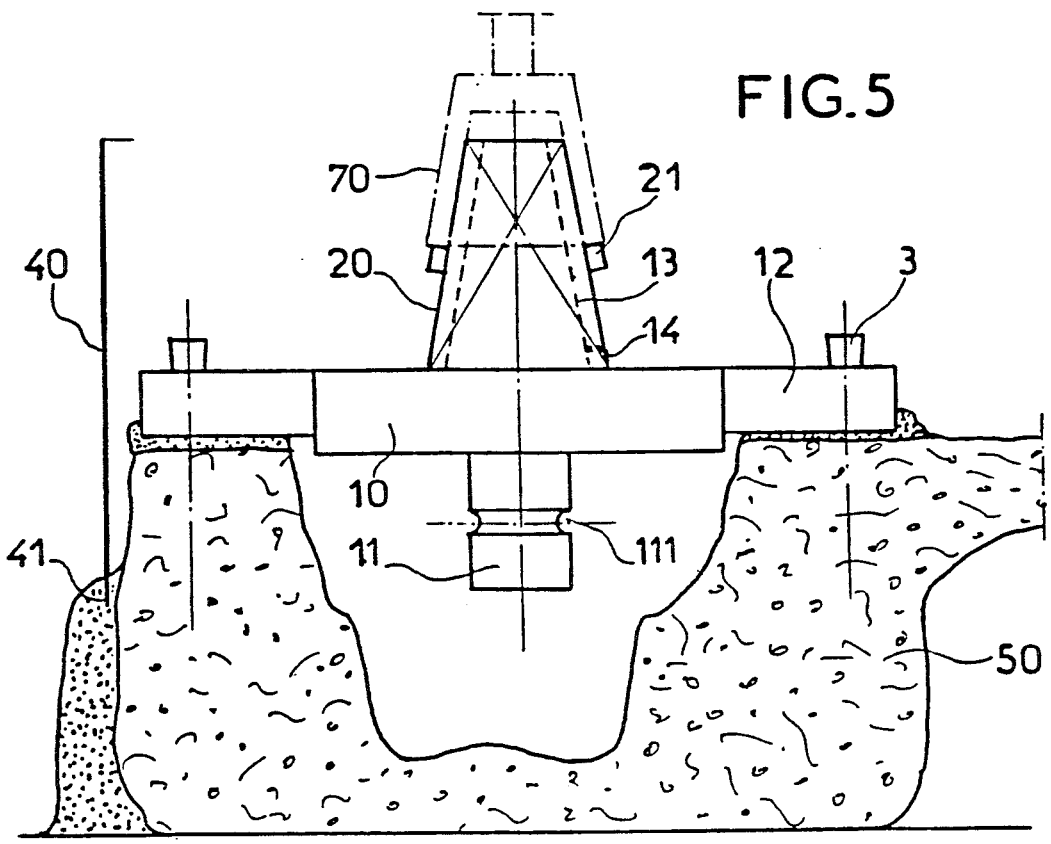
Figure 6:
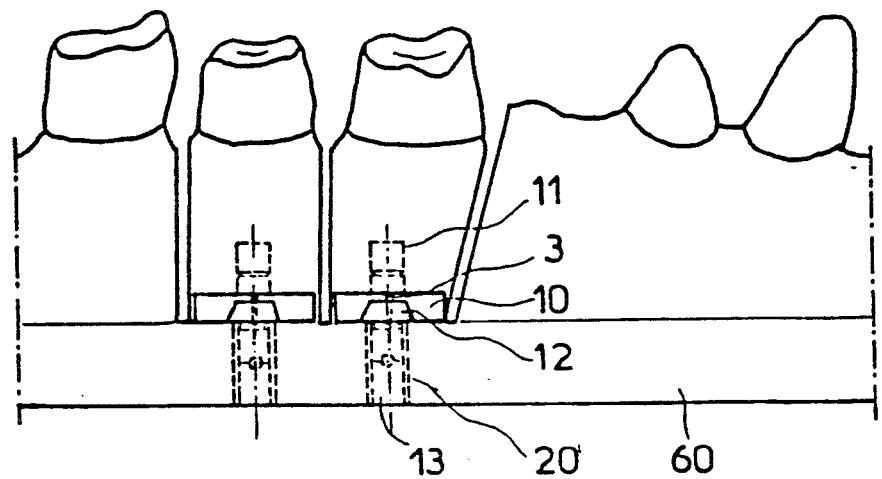
Figure 7:
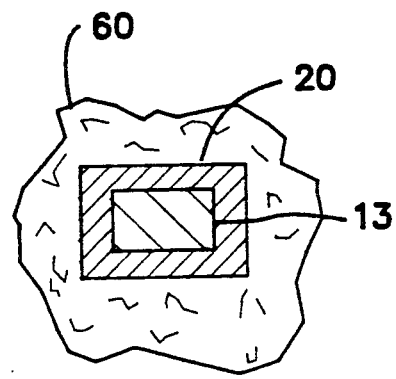
Figure 8:
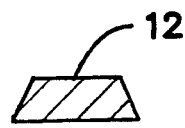

FIG. 3 shows a section of the positioning pin of the flared part with a parallelizer, FIG. 4 shows a front view of the retaining band, FIG. 5 shows a transverse section of an impression and a mold level with a prosthetic positioning device, FIG. 6 shows a partial sectioned side view of the positive mold after the saw marks have been made, FIG. 7 shows a cross sectional view along the line 7—7 of FIG. 1, and FIG. 8 shows a cross sectional view along the line 8—8 of FIG. 2.

The figures show a prosthetic positioning device for dentistry according to the invention, composed mainly of a positioning element 10 including a post 11 with a retaining groove 111, a male part 13 with a pegged tenon 14 that nests in a flared element 20 with retaining pins 21 and a pegged mortise 22, and two tongues 12 with opening 121 into which are inserted plugs 3 that join them to the side of the impression 50, as well as a band 40 with pins 41 and slots for joining 42 and 43 that has a lateral lining for the duplicate molding 60. The tongues 12 may have, for example, a trapezoidal cross section as shown in FIG. 8, where the small base of the trapezoid is on the post 11 side of the positioning element 10.

A more detailed examination of FIGS. 1, 2 and 3 shows that, considering the flared shape of the element 20 which is an integral part of the positive impression with pins 21 and with the graded section of the post 11 of the positioning element 10, these two elements can easily be joined by nesting after the mold is sawed transversely by strictly following the orientation given initially to the flared element 20 by the parallelizer, using a tip with an appropriate shape, at the time the positioning device is positioned n the negative impression, given the rectangular section (with respect to the longitudinal axis through the post 11 and male member 13, the long sides of the rectangle being orientated in the direction of the tongues 12) given to the male part 13 of the (as shown in FIG. 7) to the flared element 20 and to the presence of means of pegging 14 and 22. The elements 10 and 20 which make up the main parts of the prosthetic positioning device can therefore be joined or separated at will by simply sliding the male part 13 gently into the hollow of the flared element 20; moreover, the male parts 13 can be expelled easily from the outside, considering that the flared element 20 is flush with the duplicate molding 60. As for the tongues 12, as can be seen, they make it possible to join the positioning device to the negative impression precisely and to handle the prosthetic element 10 after sawing, alone or in combination with others. In the latter case, the ends of the tongues are connected with small bars that are assembled with adhesive or another means of this type.

It should also be noted that the two openings in the flared elements 20 make it possible to prevent them from being clogged inside with debris of the material, which can be easily eliminated, taking into account the fact that the ends of the flared elements 20 are flush with the outer side of the duplicate molding 60.

The body of the positioning element 10 may be trapezoidal in shape, depending on the position of the teeth concerned.

The process described below, illustrated by FIGS. 6 and 7, will make it easier to understand why the device is of interest compared to existing ones that are already state of the art and were mentioned in the introductory part of this description.

This process consists of:
attaching the impression 50 to a base with some modeling clay in order to immobilize it,
putting some modeling clay around the outside of the impression,
putting the prosthetic positioning devices in the impression groove, using a parallelizer equipped with a tip 70 in which the flared element 20 of the positioning device nests, until they come into contact with the pins 21,
immobilizing the positioning devices in relation to the impression by using some plugs 3 inserted into the openings 121 in the tongues 12, then pinned into the modeling clay on the rim of the impression 50,
proceeding with the prosthetic molding,
putting the band made of semi-rigid material 40 around the impression, pushing the pins 41 into the modeling clay to fix the band in the clay, then tying the two ends by overlapping the slots 42 and 43 one in the other,
pouring a duplicate mold 60 on the prosthetic mold until flush with the free end of the flared element 20,
when the setting and hardening time for the materials is over, the liner band 40 is removed and the mold of the impression is removed from the impression holder, so that the sawing operations and then disassembly can proceed,

I claim:

1. A positioner for immobilizing parts of a prosthetic dental casting and allowing molding of the casting in a single operation, said casting having a base portion and an impression portion, the impression portion being molded by an impression, the positioner comprising:
a sleeve having a tapering bore therethrough and an outer surface, the outer surface having outwardly extending protrusions for retaining said sleeve in the base portion of said casting, said bore having a rectangular cross section and the outside surface being engagable with a parallelizer for orientating said positioner, said extending protrusions limiting the engagement of said parallelizer;
a plate having opposite first and second sides;
a post protruding from said first side, said post having a groove for retaining said post in said impression portion;
a tapering male part protruding from said second side, said male part having a cross section that matches that of said tapering bore, said male part being received in said bore during casting and being removable from said bore thereafter;
a plurality of tongues extending from said plate in the general plane of said plate, said tongues retaining said positioner on the impression during casting; and a band of semi-rigid material about said impression for retaining molding material during casting.

2. A positioner according to claim 1, wherein said tongues have a trapezoidal axial cross section, the small base of said trapezoid being on the post side of the positioner.

3. A positioner according to claim 1, wherein said band is retained in modeling clay by pointed pins formed in one edge of the band at regular intervals.

4. A positioner according to claim 1, wherein said band has two ends joined by engagement of transverse slits near each said end, one slit extending inwardly from one longitudinal edge of said band, the other slit extending inwardly from the opposite longitudinal edge of the band, the length of each slot being half the width of the band.

* * * * *